(12) United States Patent
Wright et al.

(10) Patent No.: US 6,852,754 B1
(45) Date of Patent: Feb. 8, 2005

(54) BIOLOGICALLY ACTIVE LINDERAZULENE TERPENES

(75) Inventors: Amy E. Wright, Fort Pierce, FL (US); Ross E. Longley, Tallahassee, FL (US); Srinivasa Reddy Natala, Upper Darby, PA (US); John K. Reed, Ft. Pierce, FL (US)

(73) Assignee: Harbor Branch Oceanographic Institution, Inc., Fort Pierce, FL (US)

( * ) Notice: Subject to any disclaimer, the term of this patent is extended or adjusted under 35 U.S.C. 154(b) by 0 days.

(21) Appl. No.: 10/763,993

(22) Filed: Jan. 22, 2004

(51) Int. Cl.$^7$ ................ A61K 31/35; C07D 307/92
(52) U.S. Cl. ........................... 514/454; 549/458
(58) Field of Search ................. 549/458; 514/454

(56) References Cited

U.S. PATENT DOCUMENTS

| | | |
|---|---|---|
| 4,206,221 A | 6/1980 | Miller et al. |
| 4,960,790 A | 10/1990 | Stella et al. |
| 5,157,049 A | 10/1992 | Haugwitz et al. |

OTHER PUBLICATIONS

Cai, Lining and Christine D. Wu (1996) "Compounds from *Syzygium aromaticum* Processing Growth Inhibitory Activity Against Oral Pathogens" *J. Nat. Prod.* 59:987–990.

Faulkner, D. John (2000) "Marine Natural Products" *Nat. Prod. Rep.* 17:7–55.

Faulkner, D. John (2001) "Marine Natural Products" *Nat. Prod. Rep.* 18:1–49.

Faulkner, D. John (2002) "Marine Natural Products" *Nat. Prod. Rep.* 19:1–48.

Fuchs, David A. and Randall K. Johnson (Aug. 1978) "Cytologic Evidence that Taxol, an Antineoplastic Agent from *Taxus brevifolia*, Acts as a Mitotic Spindle Poison" *Cancer Treatment Reports* 62(8):1219–1222.

Fusetani, N., S. Matsunaga and S. Konosu (1981) "Bioactive marine metabolites I. Isolation of guaiazulene from the gorgonian *Euplexaura erecta*" *Experientia* 37:680–681.

Ochi, Masamitsu, Kumi Kataoka, Akira Tatsukawa, Hiyoshizo Kotsuki, Kozo Shibata (1993) "Gorgiabisazulene and Gorgiagallylazulene, Two New Guaiazulenoid Pigments from a Gorgonian *Acalycigorgia* sp." *Chemistry Letters*, pp. 2003–2006.

Rowinsky, Eric K. and Ross C. Donehower (Apr. 13, 1995) "Paclitaxel (Taxol)" *The New England Journal of Medicine* 332(15):1004–1014.

Sakemi, S. and T. Higa 1987) "2,3–Dihydrolinderazulene, a new bioactiveazulene pigment from the gorgonian *Acalycigorgia* sp." *Experientia* 43:624–625.

Schiff, Peter B., Jane Fant, Susan B. Horwitz (1979) "Promotion of microtubule assembly in vitro by taxol" *Nature* (London) 22:665–667.

Seo, Y. et al. (1996) "Isolation of GuaianoidPigments from the Gorgonian *Calicogorgia granulose*" *J. Nat. Prod.* 59:985–986.

Tanaka, Jun–ichi, Hajime Miki and Tatsuo Higa (Oct. 1992) "Echinofuran, A New Furanosequiterpene from the Gorgonian *Echinogorgia Praelonga*" *Journal of Natural Products* 55(10):1522–1524.

*Primary Examiner*—Bernard Dentz
(74) *Attorney, Agent, or Firm*—Saliwanchik, Lloyd & Saliwanchik

(57) ABSTRACT

The subject invention provides novel compositions of biologically active linderazulene terpene compounds which can advantageously be used for treating cancer and stopping cell proliferation.

21 Claims, No Drawings

BIOLOGICALLY ACTIVE LINDERAZULENE TERPENES

FIELD OF THE INVENTION

This invention relates to organic compounds and compositions which have useful therapeutic properties. More particularly, the invention concerns novel linderazulene terpene compounds having anti-proliferative and antitumor activities, pharmaceutical compositions comprising such compounds, and methods of their use for therapeutic purposes.

BACKGROUND OF THE INVENTION

Of great importance to man is the control of pathological cellular proliferation such as that which occurs in the case of cancer. Considerable research and resources have been devoted to oncology and antitumor measures including chemotherapy. While certain methods and chemical compositions have been developed which aid in inhibiting, remitting, or controlling the growth of, for example, tumors, new methods and antitumor chemical compositions are needed. Anti-proliferative agents can also be useful in treating autoimmune diseases and inflammatory disease.

In searching for new biologically active compounds, it has been found that some natural products and organisms are potential sources for chemical molecules having useful biological activity of great diversity. For example, the diterpene commonly known as paclitaxel, isolated from several species of yew trees, is a mitotic spindle poison that stabilizes microtubules and inhibits their depolymerization to free tubulin (Fuchs, D. A., R. K. Johnson [1978] *Cancer Treat. Rep.* 62:1219–1222; Schiff, P. B., J. Fant, S. B. Horwitz [1979] *Nature* (London) 22:665–667). Paclitaxel is also known to have antitumor activity and has undergone a number of clinical trials which have shown it to be effective in the treatment of a wide range of cancers (Rowinski, E. K. R. C. Donehower [1995] *N. Engl. J. Med.* 332:1004–1014). See also, e.g., U.S. Pat. Nos. 5,157,049; 4,960,790; and 4,206,221.

Marine soft corals have also proven to be a source of biologically active chemical molecules. A number of publications disclose organic compounds derived from marine soft corals including Scheuer, P. J. (ed.) *Marine Natural Products, Chemical and Biological Perspectives*, Academic Press, New York, 1978–1983, Vol. I–V; Faulkner, D. J. (2002) *Nat. Prod. Rep.* 19:1–48; Faulkner, D. J. *Nat Prod Rep.* (2001)18:1–49; Faulkner, D. J. (2000); *Nat. Prod. Rep* 17:7–55; Long B H, Carboni J M, Wasserman A J, Cornell L A, Casazza A M, Jensen P R, Lindel T, Fenical W, Fairchild C R. (1998) "Eleutherobin, a novel cytotoxic agent that induces tubulin polymerization, is similar to paclitaxel (Taxol). *Cancer Res* 58:1111–5. Some species of soft corals have proven to be rich sources of guaiazulene, inderazulene, and related sesquiterpene pigments. For example: guaizulene from the soft coral *Euplexaura erecta* (Fusetani, N.; Matsunaga, S.; Konosu, S. *Experientia* 1981, 37, 680–681); 2,3-dihydrolinderazulene, linderazulene and guiazulene from the soft coral *Acalycigorgia* sp. (Sakemi, S.; Higa, T. *Experientia* 1987, 43, 624–625; gorgiabisazulene from *Acalycigorgia* sp. (Ochi, M.; Kataoka, K; Tatsukawa, A.; Kotsuki, H.; Shibata, K.) *Chem. Lett.* 1993, 2003–2006; Echinofuran from the gorgonian *Echinogorgia praelonga* (Tanaka, J; Miki, H.; Higa, T.) *J. Nat. Prod.* 1992, 55, 1522–1524; and 2,2-biguiazulenyl from the gorgonian *Calcicorgia granuslosa* (Seo, Y.; Rho, J. R.; Geum, N.; Yoon, J. B.; Shin, J. *J. Nat. Prod.* 1996, 59, 985–986).

The prevention and control of inflammation is also often of great importance for the treatment of humans and animals. Much research has been devoted to development of compounds having anti-inflammatory properties. Certain methods and chemical compositions have been developed which aid in inhibiting or controlling inflammation, but additional anti-inflammatory methods and compositions are needed.

Neuroinflammatory conditions are complex and poorly understood disease processes. Mononuclear-phagocytes become activated in a number of inflammatory conditions, such as neurogenic inflammation, meningitis, septic shock, Down's syndrome, postischemic brain injury, HIV encephalopathy, Parkinson's disease, Alzheimer's disease, amyotrophic lateral sclerosis and multiple sclerosis (Mayer, A. M. [1988] Medicina. (B. Aires.) 58:377–385). Present therapies for these and other inflammatory conditions are based on steroids and nonsteroidal anti-inflammatory compositions which are usually associated with a high incidence of unsatisfactory toxicity and poor efficacy (Faden, A. I. and S. Salzman [1992] Trend in Pharmacological Sciences 13:29–35).

Immunomodulation is a developing segment of immunopharmacology. Immunomodulator compounds and compositions, as the name implies, are useful for modulating or regulating immunological functions in animals. Immunomodulators may be immunostimulants for building up immunities to, or initiate healing from, certain diseases and disorders. Conversely, immunomodulators may be immunoinhibitors or immunosuppressors for preventing undesirable immune reactions of the body to foreign materials, or to prevent or ameliorate autoimmune reactions or diseases.

Immunomodulators have been found to be useful for treating systemic autoimmune diseases, such as lupus erythematosus and diabetes, as well as immunodeficiency diseases. Further, immunomodulators may be useful for immunotherapy of cancer or to prevent rejections of foreign organs or other tissues in transplants, e.g., kidney, heart, or bone marrow.

Various immunomodulator compounds have been discovered, including FK506, muramylic acid dipeptide derivatives, levamisole, niridazole, oxysuran, flagyl, and others from the groups of interferons, interleukins, leukotrienes, corticosteroids, and cyclosporins. Many of these compounds have been found, however, to have undesirable side effects and/or high toxicity. New immunomodulator compounds are therefore needed to provide a wider range of immunomodulator function.

BRIEF SUMMARY OF THE INVENTION

The subject invention provides novel compounds having advantageous biological activity.

These compounds can be used in the treatment of a number of conditions in which aberrant cellular proliferation occurs. These conditions include, for example, tumors and other forms of cancer, autoimmune disorders and inflammatory diseases.

In a preferred embodiment, the subject invention provides novel compositions of biologically active linderazulene analogs which have utility for use in the treatment of cancer. The subject invention further provides advantageous methods of use for the novel compounds and compositions.

In a specific embodiment, the novel compositions and methods of the subject invention can be used in the treatment of an animal hosting cancer cells including, for example, inhibiting the growth of tumor cells in a mammalian host.

More particularly, the subject compounds can be used for inhibiting in a human the growth of tumor cells, including cells of breast, colon, CNS, ovarian, renal, prostate, liver, pancreatic, uterine, or lung tumors, as well as human leukemia or melanoma cells. The mechanisms for achieving anticancer activity exhibited by the subject compounds would lead a person of ordinary skill in the art to recognize the applicability of the subject compounds, compositions, and methods to additional types of cancer as described herein.

In accordance with the subject invention, methods for inhibiting cancer cells in a host include contacting tumor cells with an effective amount of the new pharmaceutical compositions of the invention. The cancer cells inhibited by the invention are those which are susceptible to the subject compounds described herein or compositions comprising those compounds.

In specific embodiments, the subject invention provides two new terpenes, 11-carbomethoxylinderazulene (I) and 11-formyllinderazulene (II). The compounds of the subject invention have not been isolated previously from a natural source nor have they been previously synthesized.

Additional aspects of the invention include the provision of methods for producing the new compounds and compositions.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

DETAILED DISCLOSURE OF THE INVENTION

The subject invention provides novel compositions of biologically active linderazulene compounds that are useful for inhibiting unwanted cellular proliferation. Thus, the compounds of the subject invention for treating cancer, as well as for immunomodulation and in the control of inflammation. In a specific embodiment, the novel compounds, compositions and methods of use can advantageously be used to inhibit the growth of tumor and other cancer cells in a mammalian host.

As described herein, the compounds of the subject invention have utility for use in the treatment of cancer. More particularly, the subject compounds can be used for inhibiting in a human the growth of tumor cells, including cells of breast, prostate, colon, CNS, ovarian, renal, liver, pancreatic, uterine, or lung tumors, as well as human leukemia or melanoma cells. The compounds also have utility in the treatment of multi-drug resistant cancer cells.

In accordance with the invention, methods for inhibiting cancer in a host include contacting cancer cells with an effective amount of the new pharmaceutical compositions of the invention. The tumor cells inhibited by the invention are those which are susceptible to the subject compounds described herein or compositions comprising those compounds.

The subject invention further provides methods of use of the new compounds and compositions of the invention, e.g., methods of inhibiting tumors and other cancer cells in an animal, preferably a mammal. Most preferably, the invention comprises a method for the antitumor treatment of a human in need of such treatment, i.e., a human hosting cancer cells, including breast, colon, liver, pancreatic, uterine, or lung tumor cells, or leukemia cells including multi-drug resistant cancer cells.

In preferred embodiments, the compounds of the subject invention have the following structural formula:

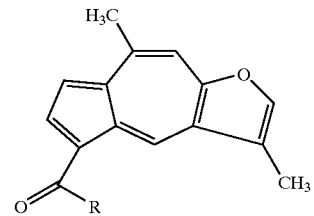

wherein R is selected from the group consisting of H, $OR_1$, and $NZ_1Z_2$;

$R_1$ is selected from H, $C_1$ to $C_8$ alkyl, phenyl, substituted aryl or benzyl;

$Z_1$ and $Z_2$ are the same or different and independently chosen from the group consisting of H, $C_1$ to $C_8$ alkyl, phenyl, substituted aryl, or wherein $NZ_1Z_2$ represents an amino acid which is linked to the linderazulene nucleus via the nitrogen to form a peptide bond; or a salt of said compound.

In specific embodiments the current invention provides the novel compounds 11-carbomethoxylinderazulene (I) and 11-formyllinderazulene (II). Advantageously 11-carbomethoxylinderazulene (I) and 11-formyllinderazulene can inhibit proliferation of tumor cell lines.

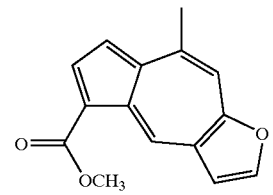

11-carbomethoxy linderazulene (I)

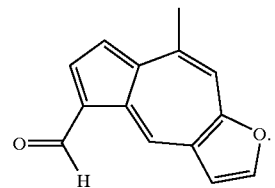

11-formyllinderazulene (II)

In additional specific embodiments, the subject invention provides compounds that are hydrazone or semicarbazone derivative of 11-formyl linderazulene (I).

In preferred embodiments of the invention, the compounds are substantially pure, i.e., contain at least 95% of the compound as determined by established analytical methods.

In further preferred methods of the invention, salts within the scope of the invention are made by adding mineral acids, e.g., HCl, $H_2SO_4$, or strong organic acids, e.g., formic, oxalic, in appropriate amounts to form the acid addition salt of the parent compound or its derivative. Also, synthesis type reactions may be used pursuant to known procedures to add or modify various groups in the preferred compounds to produce other compounds within the scope of the invention.

The scope of the invention is not limited by the specific examples and suggested procedures and uses related herein since modifications can be made within such scope from the information provided by this specification to those skilled in the art.

As used in this application, the terms "analogs," refers to compounds which are substantially the same as another compound but which may have been modified by, for example, adding or removing side groups.

In one embodiment, the subject invention pertains to the immunosuppressive use of the subject compounds. These compounds can be used to reduce, suppress, inhibit, or prevent unwanted immune responses. Thus, the compounds of the subject invention are useful for treatments of humans or animals requiring immunosuppression. Examples of conditions for which immunosuppression is desired include, but are not limited to, treatment or prevention of autoimmune diseases such as diabetes, lupus, and rheumatoid arthritis. Immunosuppression is also frequently needed in conjunction with organ transplants. Immunosuppressive agents can also be utilized when a human or animal has been, or may be, exposed to superantigens or other factors known to cause overstimulation of the immune system. The compounds of the subject invention are also useful as standards to assess the activity of other putative immunosuppressive agents.

The invention also comprises anti-inflammatory pharmaceutical compositions, e.g. anti-inflammatory compositions, containing as an active ingredient an effective amount of one or more compounds described herein and a non-toxic, pharmaceutically acceptable carrier or diluent. The pharmaceutical compositions of the subject invention can further comprise other active compounds. Such other active compounds include, but are not limited to, other anti-inflammatory compounds for example, steroidal compounds, including hydrocortisone and the like; or non-steroidal anti-inflammatories, including acetylsalicylic acid (aspirin), ibuprofen, acetaminophen, indomethacin, and the like. The second active ingredient can include antiviral, antibacterial, antifungal or other antimicrobial compounds or antitumor compounds as well.

For purposes of the subject invention, unless otherwise noted, the terms "inflammation" and "inflammatory response" include any and all reactions including, but not limited to, immune-related responses and/or allergic reactions to a physical, chemical, or biological stimulus. "Anti-immune-mediated" and anti-neurogenic inflammatory activity," as used herein, will be understood by those of ordinary skill in the art to mean biological activity inhibiting or controlling an immune-mediated and/or neurogenic inflammatory response. Inflammation for which the primary activating inflammation is antigen-derived can be due to, for example, bacterial lipopolysaccharide.

The compounds and compositions of the subject invention can be used in the treatment of inflammation at sites where the primary activating factor is antigen-derived (e.g. bacterial lipopolysaccharide) or of neurogenic origin. Thus, the compounds of the subject invention can be used to treat conditions including, but not limited to, neurogenic inflammation, meningitis, septic shock, Down's syndrome, postischemic brain injury, HIV encephalopathy, Parkinson's disease, Alzheimer's disease, amyotrophic lateral sclerosis and multiple sclerosis.

The subject compounds and compositions can also be useful in the treatment of chronic pain, migraines, thermal-induced pain, such as sunburn, or other thermal and nociceptive pain, and chronic pain associated with arthritis. Uses can also include other inflammatory conditions that involve a neurogenic pain-producing component, e.g., certain metastatic carcinomas or inflammation of the blood vessels.

The compounds of the subject invention can also be used to treat allergic responses and/or promote wound healing. This can include the use of the compounds in aerosol form for the treatment of acute allergic reactions such as acute asthmatic attack and in the treatment of inflammation of the lung caused by chemical exposure.

The compounds of the subject invention can also be used to treat conjunctivitis, inflammatory gum diseases, inflammatory bowel disease, and nephritis.

A more complete understanding of the invention can be obtained by reference to the following specific examples of compounds, compositions, and methods of the invention. The following examples illustrate procedures for practicing the invention. These examples should not be construed as limiting. All percentages are by weight and all solvent mixture proportions are by volume unless otherwise noted. It will be apparent to those skilled in the art that the examples involve use of materials and reagents that are commercially available from known sources, e.g., chemical supply houses, so no details are given respecting them.

EXAMPLE 1

Collection and Taxonomy of the Source Organism

The gorgonian specimen (HBOI ID # 19-V-00-3-003) was collected using Harbor Branch Oceanographic Institution's Johnson-Sea-Link research submersible off the northwest coast of Curacao, 12° 22.78' N latitude and 69° 10.15' W longitude, on a rocky slope and at a depth of 342 m. The specimen was frozen immediately after collection and kept frozen until workup. This specimen most closely fits the genus *Paramuricea* Kölliker, 1865 [Cnidaria, Anthozoa, Gorgonacea, Plexauridae (Paramuriceidae)], but can not be ascribed to a known species at this time. It differs from other specimens that were collected in the same region, in both morphology and spiculation. This holaxonian gorgonian specimen was 40 cm tall, 30 cm wide, and branching mostly in one plane. The base of the main stem is 6 mm diameter, which has several secondary branches and numerous short (1–2 cm) terminal branchlets, 0.5–0.75 mm diameter, which do not anastomose. The polyps are distributed over the entire surface, tend to alternate about 1–2 mm apart, and are denser on the branchlets. The calyces (anthostele) are tubular to conical, ~0.5 mm high, and consist of relatively few thorn scale spicules with very blunt, slightly spinous, projecting spine and sparse basal root. The large anthocodia are exert (1–2 mm), with long tentacles and pinnules. The anthocodial collaret is relatively strong with a crown of 3–4 rows of thin, curved, slightly spinous spindles and some spinose rods. The coenenchyme consists of a thin layer of spicules, dominated by knee-shaped rods that are warty on the convex side and smooth on the concave side, and a few crosses. The axis is soft and fibrous with a cross-chambered central core. The coenenchymal spicules range from ~0.07 to 0.20 mm in length; the thorn scales are ~0.25 mm; the anthocodial spindles are ~0.15 to 0.45 mm; and the anthocodial rods are ~0.23 to 0.30 mm. The color of the specimen was described in situ from the submersible as pale lavender. While still fresh in the lab, the main stalk and branches were pale lavender, and the branchlets were tan. In alcohol the specimen is dark brown. A museum voucher specimen is deposited at the Harbor Branch Oceanographic Museum, catalog number 012:00804.

EXAMPLE 2

Isolation of 11-carbomethoxylinderazulene (I) and 11-formylinderazulene (II)

A frozen specimen of the gorgonian (100 g wet wt) was chopped into small slices and extracted exhaustively with EtOH (3×400 mL). The combined EtOH extracts were concentrated by distillation under reduced pressure. The resulting residue was partitioned between water and EtOAc (3×100 mL). The combined EtOAc partition was concentrated to yield 1.2 g of a reddish brown solid. This residue was fractionated by vacuum column chromatography on a Kieselgel 60H stationary phase using a step gradient of EtOAc in heptane. The fractions which eluted with heptane and heptane-EtOAc 95:5 (v/v) were combined and chromatographed by reversed phase HPLC [Vydac C-18 Protein and Peptide column, 10×250 mm, $H_2O$: $CH_3CN$ 2:8, flow rate=3 ml/min, detected by UV absorbance at 254 nm] to yield compounds I (21 mg, 0.021% yield of wet wt.) and II (1.2 mg, 0.0012% yield of wet wt.).

11-Carbomethoxylinderazulene (I): amorphous pink solid, mp 138–139° C.; WV (MeOH) $\lambda_{max}$ ($\epsilon$) 389 (8282), 376 (6381), 325 (11880), 308 (20367), 247 (10048), 228 (11270) run; IR (NaCl neat) $v_{max}$ 2946, 2918, 2853, 1678, 1447, 1408, 1387, 1305, 1217, 1188, 1133, 1079, 1056, 939 $cm^{-1}$; $^1H$ and $^{13}C$ NMR data are given in Table 1. HRFABMS m/z: 255.1033 (calcd for $C_{16}H_{15}O_3$ $[M+H]^+$, 255.1021).

11-Formyllinderazulene (II): amorphous pink solid, mp 136° C.; UV (MeOH) $\lambda_{max}$ (log $\epsilon$) 395 (7308), 332 (9385), 316 (13308), 293 (10615), 260 (14284), 215 (12077) run; IR (NaCl neat) $v_{max}$ 2956, 2923, 2853, 2746, 1641, 1634, 1398, 1374, 1297, 1286, 1233, 1148, 1081, 1044, 943 $cm^{-1}$; $^1H$ and $^{13}C$ NMR data are given in Table 2; HRFABMS m/z: 225.0917 (calcd for $C_{15}H_{13}O_2$ $[M+H]^+$, 225.0915).

TABLE 1

NMR Spectral Data for 11-carbomethoxylinderazulene (I) in $CDCl_3$.

| Position | $^{13}C$ $\delta$, mult. | $^1H$ $\delta$ (mult., J in Hz) | HMBC[a] | NOESY |
|---|---|---|---|---|
| 2 | 141.1 d | 7.56 (s) | C-3, C-3a, C-9a | H-10 |
| 3 | 120.3 s | | | |
| 3a | 126.3 s | | | |
| 4 | 130.7 d | 9.99 (s) | C-3a, C-4a, C-7a, C-9a | H-10 |
| 4a | 116.4 s | | | |
| 5 | 136.3 s | | | |
| 6 | 137.0 d | 8.24 (d, 3.7) | C-4a, C-5, C-7a | H-7 |
| 7 | 116.1 d | 7.28 (d, 3.7) | C-4a, C-5, C-6, C-7a | H-6 H-12 |
| 7a | 139.3 s | | | |
| 8 | 141.1 s | | | |
| 9 | 115.7 d | 7.69 (s) | C-3a, C-7a, C-8, C-9a, C-12 | H-12 |
| 9a | 159.1 s | | | |
| 10 | 8.0 q | 2.45 (s, 3H) | C-2, C-3, C-3a | H-4, H-2 |
| 11 | 166.3 s | | | |
| 12 | 25.2 q | 2.93 (s, 3H) | C-7a, C-8, C-9 | H-7, H-9 |
| —$OCH_3$ | 50.9 q | 3.94 (s, 3H) | C-11 | |

[a]HMBC Correlation from H number to carbon atoms listed

TABLE 2

NMR Spectral Data for 11-formyllinderazulene (II) in $CDCl_3$.

| Position | $^{13}C$ ($\delta$, mult.) | $^1H$ $\delta$ (mult., J in Hz) | HMBC[a] | NOESY |
|---|---|---|---|---|
| 2 | 141.8 d | 7.56 (s) | C-3, C-3a, C-9a | H-10 |
| 3 | 120.5 s | | | |
| 3a | 126.6 s | | | |
| 4 | 131.5 d | 9.99 (s) | C-3a, C-4a, C-7a, C-9a | H-10 |
| 4a | 117.4 s | | | |
| 5 | 135.1 s | | | |
| 6 | 141.3 d | 8.09 (d, 3.7) | C-4a, C-5, C-7a | H-7 |
| 7 | 117.6 d | 7.32 (d, 3.7) | C-4a, C-5, C-6, C-7a | H-6, H-12 |
| 7a | 141.7 s | | | |
| 8 | 141.5 s | | | |
| 9 | 117.4 d | 7.80 (s) | C-3a, C-7a, C-8, C-9a, C-12 | H-12 |
| 9a | 159.4 s | | | |
| 10 | 8.0 q | 2.46 (s, 3H) | C-2, C-3, C-3a | H-4, H-2 |
| 11 | 187.1 d | 10.29 (s) | C-5 | |
| 12 | 25.2 q | 2.94 (s, 3H) | C-7a, C-8, C-9 | H-7, H-9 |

[a]HMBC Correlation from H number to carbon atoms listed

EXAMPLE 3

Antitumor Effects of 11-carbomethoxylinerazulene (I) and 11-formylinerazulene (II)

Compounds I and II was analyzed as to their effect on the proliferation of PANC-1 human pancreatic and P388 murine leukemia cell lines. P388 cells were obtained from Dr. R. Camalier, National Cancer Institute, Bethesda, Md., and PANC-1 cells were obtained from American Type Culture Collection, Rockville, Md. All cell lines were maintained in tissue culture medium (TCM; Roswell Park Memorial Institute RPMI 1640 supplemented with 100 U/mL penicillin, 100 mg/mL streptomycin, 60 mg/mL 1-glutamine, 18 mM HEPES, 0.05 mg/mL gentamicin (Life Technologies, Gaithersburg, Md.) and 10% fetal bovine serum) and cultured in plastic tissue culture flasks at 37° C. in humidified air containing 5% $CO_2$. Stock cultures of P388 cells were subcultured 1:20 in fresh TCM every 2 to 3 days. Stock cultures of A549 cells were subcultured 1:10 every 3 to 4 days. To assess the antiproliferative effects of agents against the cells, 200 mL cultures (96-well tissue culture plates, Nunc, Denmark) were established at 1×$10^5$ cells/mL in TCM or TCM containing the test agent at 0.03–5.0 $\mu$g/mL. After 48-h exposures, P388 cells were enumerated using 3-[4,5-dimethylthiazol-2-yl]-2,5-diphenyltetrazolium bromide (MTT) as described in the literature (M. C. Alley, et al., Cancer Res. 48:589, 1988). PANC-1 cells were enumerated in the same manner after 72 hours exposure. The results were expressed as percent inhibition compared to the negative (no drug) control. Positive drug controls of varying dilutions of 5-fluorouracil and adriamycin (Sigma Chemical Co., St Louis, Mo.) were included to monitor drug sensitivity of the cell line.

To quantitate the effects on cell proliferation and resulting $IC_{50}$ values, 75 mL of warm growth media containing 5 mg/mL MTT is added to each well, cultures returned to the incubator, and left undisturbed for 3 hours. To spectrophotometrically quantitate formation of reduced formazan, plates are centrifuged (500×g, 10 minutes), culture fluids removed by aspiration, and 200 $\mu$l of acidified isopropanol (2 mL concentrated HCl/liter isopropanol) added per well. The absorbance of the resulting solutions is measured in a plate reader (TECAN Spectra SLT; TECAN U.S., Research Triangle Park, N.C.) at 570 nm and a 650 nm reference filter. The absorbance of test wells is divided by the absorbance of drug-free wells, and the concentration of agent that results in 50% of the absorbance of untreated cultures ($IC_{50}$) is determined by linear regression of logit-transformed data (D. J. Finney, Statistical Method in Biological Assay, third ed., pp.316–348, Charles Griffin Co., London, 1978). A linear relationship between tumor cell number and formazan production has been routinely observed over the range of cell densities observed in these experiments. The two standard drug controls (indicated above) are included in each assay as a check to monitor the drug sensitivity of each of the cell lines and $IC_{50}$ values are determined for each drug-cell combination.

A summary of results in this assay for compounds I and II can be found in Table 3. Table 3. In vitro activity of compounds I and II against tumor cell lines.

|  | PANC-1 ($IC_{50}$ µg/ml) | P388 ($IC_{50}$ µg/ml) |
|---|---|---|
| 11-carbomethoxylinderazulene (I) | 18.7 | 2.7 |
| 11-formyllinderazulene (II) | No inhibition of cell proliferation detected at 50 µg/ml under the conditions tested | 15.6 |

EXAMPLE 4

Formulation and Administration

The compounds of the invention are useful for various non-therapeutic and therapeutic purposes. It is apparent from the testing that the compounds of the invention are effective for inhibiting cell growth and/or proliferation. Because of the antiproliferative properties of the compounds, they are useful to prevent unwanted cell growth in a wide variety of settings including in vitro uses. They are also useful as standards and for teaching demonstrations. As disclosed herein, they are also useful prophylactically and therapeutically for treating cancer cells in animals and humans.

Therapeutic application of the new compounds and compositions containing them can be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the cells that are to be inhibited, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A compound having the following structural formula:

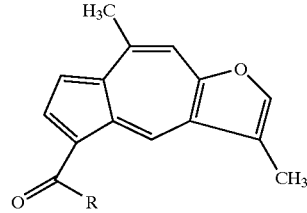

wherein R is selected from the group consisting of H, $OR_1$, and $NZ_1Z_2$;

$R_1$ is selected from the group consisting of H, $C_1$ to $C_8$ alkyl, phenyl, substituted aryl and benzyl;

$Z_1$ and $Z_2$ are the same or different and independently chosen from the group consisting of H, $C_1$ to $C_8$ alkyl, phenyl, substituted aryl, or wherein $NZ_1Z_2$ represents an amino acid which is linked to the linderazulene nucleus via the nitrogen to form a peptide bond; or a salt thereof.

2. The compound, according to claim 1, selected from the group consisting of 11-carbomethoxylinderazulene (I), 11-formyl linderazulene (II), and salts thereof.

3. The compound, according to claim 1, wherein $R=OCH_3$.

4. The compound, according to claim 1, wherein R=H.

5. The compound, according to claim 1, wherein the compound is a hydrazone or semicarbazone derivative of 11-formyl linderazulene (I).

6. The compound, according to claim 1, having the following spectroscopic properties: UV (MeOH)) $\lambda_{max}$ (ε) 389 (8282), 376 (6381), 325 (11880), 308 (20367), 247 (10048), 228 (11270) nm; IR (NaCl neat) $v_{max}$ 2946, 2918, 2853, 1678, 1447, 1408, 1387, 1305, 1217, 1188, 1133, 1079, 1056, 939 $cm^{-1}$; HRFABMS m/z: 255.1033 (calcd for $C_{16}H_{15}O_3$ $[M+H]^+$, 255.1021); $^{13}C$ (observed at 125 MHz in $CDCl_3$) δ 166.3 s; 159.1 s, 141.1 s, 141.1 d, 139.3 s, 137.0 d, 136.3 s, 130.7 d, 126.3 s, 120.3 s, 116.4 s, 116.1 d, 115.7 d, 50.9 q, 25.2 q, and 8.0 q; $^1H$ NMR (observed at 500 MHz in $CDCl_3$) δ 2.45 (s, 3H), 2.93 (s, 3H), 3.94 (s, 3H), 7.28 (d, 3.7), 7.56 (s), 7.69 (s), 8.24 (d, 3.7), 9.99 (s).

7. The compound, according to claim 1, having the following spectroscopic properties: UV (MeOH) $\lambda_{max}$ (log $\epsilon$) 395 (7308), 332 (9385), 316 (13308), 293 (106115), 260 (14284), 215 (12077) nm; IR (NaCl neat) $\nu_{max}$ 2956, 2923, 2853, 2746, 1641, 1634, 1398, 1374, 1297, 1286, 1233, 1148, 1081, 1044, 943 cm$^{-1}$; HFABMS m/z: 225.0917 (calcd for $C_{15}H_{13}O_2$ [M+H]$^+$, 225.0915); $^{13}C$ (observed at 125 MHz in CDCl$_3$) 187.1 d, 159.4 s, 141.8 d, 141.7 s, 141.5 s, 141.3 d, 135.1 s, 131.5 d, 126.6 s, 120.5 s, 117.6 d, 117.4 s, 117.4 d, 25.2 q, 8.0 q; $^1H$ NMR (observed at 500 MHz in CDCl$_3$) 10.29 (s), 9.99 (s), 8.09 (d, 3.7), 7.80 (s), 7.56 (s), 7.32 (d, 3.7), 2.94 (s, 3H), 2.46 (s, 3H).

8. A method for inhibiting cellular proliferation, said method comprising administering to a patient in need of such treatment an effective amount of a compound having the following structure:

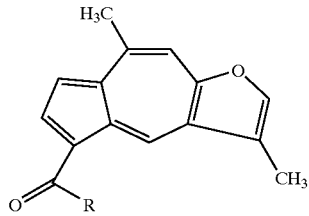

wherein R is selected from H, OR$_1$, or NZ$_1$Z$_2$;

R$_1$ is selected from the group consisting of H, C$_1$ to C$_8$ alkyl, phenyl, substituted aryl and benzyl; and Z$_1$ and Z$_2$ are the same or different and independently chosen from the group consisting of H, C$_1$ to C$_8$ alkyl, phenyl, substituted aryl or wherein NZ$_1$Z$_2$ represents an amino acid which is linked to the linderazulene nucleus via the nitrogen to form a peptide bond; or a salt of said compound.

9. The method, according to claim 8, wherein R=OCH$_3$.

10. The method, according to claim 8, wherein R=H.

11. The method, according to claim 8, wherein the compound is a hydrazone or semicarbazone derivative of 11-formyl linderazulene (I).

12. The method, according to claim 8, wherein said compound has the following spectroscopic properties: UV (MeOH) $\lambda_{max}$ ($\epsilon$) 389 (8282), 376 (6381), 325 (11880), 308 (20367), 247 (10048), 228 (11270) nm; IR (NaCl neat) $\nu_{max}$ 2946, 2918, 2853, 1678, 1447, 1408, 1387, 1305, 1217, 1188, 1133, 1079, 1056, 939 cm$^{-1}$; HRFABMS m/z: 255.1033 (calcd for $C_{16}H_{15}O_3$ [M+H]$^+$, 255.1021); $^{13}C$ (observed at 125 MHz in CDCl$_3$) $\delta$ 166.3 s; 159.1 s, 141.1 s, 141.1 d, 139.3 s, 137.0 d, 136.3 s, 130.7 d, 126.3 s, 120.3 s, 116.4 s, 116.1 d, 115.7 d, 50.9 q, 25.2 q, and 8.0 q; $^1H$ NMR (observed at 500 MHz in CDCl$_3$) $\delta$ 2.45 (s, 3H), 2.93 (s, 3H), 3.94 (s, 3H), 7.28 (d, 3.7), 7.56 (s), 7.69 (t), 8.24 (d, 3.7), 9.99 (s).

13. The method, according to claim 8, wherein said compound has the following spectroscopic properties: UV (MeOH) $\lambda_{max}$ (log $\epsilon$) 395 (7308), 332 (9385), 316 (13308), 293 (10615), 260 (14284), 215 (12077) nm; IR (NaCl neat) $\nu_{max}$ 2956, 2923, 2853, 2746, 1641, 1634, 1398, 1374, 1297, 1286, 1233, 1148, 1081, 1044, 943 cm$^{-1}$; HRFABMS m/z: 225.0917 (calcd for $C_{15}H_{13}O_2$ [M+H]$^+$, 225.0915); $^{13}C$ (observed at 125 MHz in CDCl$_3$) 187.1 d, 159.4 s, 141.8 d, 141.7 s, 141.5 s, 141.3 d, 135.1 s, 131.5 d, 126.6 s, 120.5 s, 117.6 d, 117.4 s, 117.4 d, 25.2 q, 8.0 q; $^1H$ NMR (observed at 500 MHz in CDCl$_3$) 10.29 (s), 9.99 (s), 8.09 (d, 3.7), 7.80 (s), 7.56 (s), 7.32 (d, 3.7), 2.94 (s, 3H), 2.46 (s, 3H).

14. The method, according to claim 8, wherein said cellular proliferation is associated with a condition selected from the group consisting of autoimmune disorders, inflammation, tumors and cancer.

15. The method, according to claim 14 wherein said cancer is selected from the group consisting of breast cancer, colon cancer, CNS cancer, liver cancer, lung cancer, leukemia, melanoma, ovarian cancer, uterine cancer, renal cancer, pancreatic cancer and prostate cancer.

16. A pharmaceutical composition comprising a compound having the following structure:

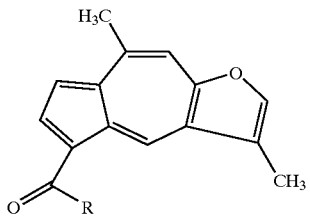

wherein R is selected from H, OR$_1$, and NZ$_1$Z$_2$,

R$_1$ is selected from the group consisting of H, C$_1$ to C$_8$ alkyl, phenyl, substituted aryl and benzyl; and Z$_1$ and Z$_2$ are the same or different and independently chosen from the group consisting of H, C$_1$ to C$_8$ alkyl, phenyl, substituted aryl or wherein NZ$_1$Z$_2$ represents an amino acid which is linked to the linderazulene nucleus via the nitrogen to form a peptide bond; or a salt of said compound wherein said composition further comprises a pharmaceutically acceptable carrier.

17. The pharmaceutical composition, according to claim 16 comprising a compound in which R=OCH$_3$.

18. The pharmaceutical composition, according to claim 16 comprising a compound in which R=H.

19. The pharmaceutical composition, according to claim 16, comprising a compound which is a hydrazone or semicarbazone derivative of 11-formyl linderazulene (I).

20. The composition, according to claim 16, comprising a compound with the following spectroscopic properties: UV (MeOH) $\lambda_{max}$ ($\epsilon$) 389 (8282), 376 (6381), 325 (11880), 308 (20367), 247 (10048), 228 (11270) nm; IR (NaCl neat) $\nu_{max}$ 2946, 2918, 2853, 1678, 1447, 1408, 1387, 1305, 1217, 1188, 1133, 1079, 1056, 939 cm$^{-1}$; HRFABMS m/z: 255.1033 (calcd for $C_{16}H_{15}O_3$ [M+H]$^+$, 255.1021); $^{13}C$ (observed at 125 MHz in CDCl$_3$) $\delta$ 166.3 s, 159.1 s, 141.1 s, 141.1 d, 139.3 s, 137.0 d, 136.3 s, 130.7 d, 126.3 s, 120.3 s, 116.4 s, 116.1 d, 115.7 d, 50.9 q, 25.2 q, and 8.0 q; $^1H$ NMR (observed at 500 MHz in CDCl$_3$) $\delta$ 2.45 (s, 3H), 2.93 (s, 3H), 3.94 (s, 3H), 7.28 (d, 3.7), 7.56 (s), 7.69 (s), 8.24 (d, 3.7), 9.99 (s).

21. The composition, according to claim 16, comprising a compound with the following spectroscopic properties: UV (MeOH) $\lambda_{max}$ (log $\epsilon$) 395 (7308), 332 (9385), 316 (13308), 293 (10615), 260 (14284), 215 (12077) nm; IR (NaCl neat) $\nu_{max}$ 2956, 2923, 2853, 2746, 1641, 1634, 1398, 1374, 1297, 1286, 1233, 1148, 1081, 1044, 943 cm$^{-1}$; HRFABMS m/z: 225.0917 (calcd for $C_{15}H_{13}O_2$ [M+H]$^+$, 225.0915); $^{13}C$ (observed at 125 MHz in CDCl$_3$) 187.1 d, 159.4 s, 141.8 d, 141.7 s, 141.5 s, 141.3 d, 135.1 s, 131.5 d, 126.6 s, 120.5 s, 117.6 d, 117.4 s, 117.4 d, 25.2 q, 8.0 q; $^1H$ NMR (observed at 500 MHz in CDCl$_3$) 10.29 (s), 9.99 (s), 8.09 (d, 3.7), 7.80 (s), 7.56 (s), 7.32 (d, 3.7), 2.94 (s, 3H), 2.46 (s, 3H).

* * * * *

UNITED STATES PATENT AND TRADEMARK OFFICE
CERTIFICATE OF CORRECTION

PATENT NO. : 6,852,754 B1
DATED : February 8, 2005
INVENTOR(S) : Wright et al.

It is certified that error appears in the above-identified patent and that said Letters Patent is hereby corrected as shown below:

Column 1,
Line 38, "WV(MeOH)" should read -- UV(MeOH) --.
Line 67, "(11270) run;" should read -- (11270) nm; --.

Column 3,
Line 66, "(12077) run;" should read -- (12077) nm; --.

Column 5,
Line 46, "A summary of results in this assay for compounds I and II can be found in Table 3. Table 3. In vitro activity of compounds I and II against tumor cell lines." should read -- A summary of results in this assay for compounds I and II can be found in Table 3.
Table 3. In vitro activity of compounds I and II against tumor cell lines. --.
Line 48, "HFABMS" should read -- HRFABMS --.
Line 52, "7.69(t)," should read -- 7.69(s), --.
Line 55, "WV(MeOH)" should read -- UV(MeOH) --.
Line 58, "(11270) run;" should read -- (11270) nm; --.
Line 65, "(12077) run;" should read -- (12077) nm; --.

Column 6,
Line 2, "WV(MeOH)" should read -- UV(MeOH) --.
Line 11, "(11270) run;" should read -- (11270) nm; --.
Line 18, "(12077) run;" should read -- (12077) nm; --.
Line 47, "(11270) run;" should read -- (11270) nm; --.
Line 58, "(12077) run;" should read -- (12077) nm; --.

Signed and Sealed this

Fifteenth Day of November, 2005

JON W. DUDAS
*Director of the United States Patent and Trademark Office*